United States Patent
May et al.

(10) Patent No.: US 8,254,650 B2
(45) Date of Patent: Aug. 28, 2012

(54) SYSTEM AND METHOD FOR CONTRAST ENHANCEMENT OF TIME-RESOLVED FLUORESCENCE IMAGES

(75) Inventors: Andrzej May, Schenectady, NY (US); Siavash Yazdanfar, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 819 days.

(21) Appl. No.: 12/394,381

(22) Filed: Feb. 27, 2009

(65) Prior Publication Data
US 2010/0220903 A1  Sep. 2, 2010

(51) Int. Cl.
*G06K 9/00* (2006.01)

(52) U.S. Cl. ........ 382/128; 382/129; 382/130; 382/131; 382/294; 382/191; 382/216; 382/217; 382/218; 382/278; 600/410; 600/436; 600/458; 378/44

(58) Field of Classification Search .......... 382/128–131, 382/294, 191, 216–218, 278; 600/410, 436, 600/458; 378/44
See application file for complete search history.

(56) References Cited

U.S. PATENT DOCUMENTS

| | | | |
|---|---|---|---|
| 4,840,485 A | | 6/1989 | Gratton |
| 4,907,156 A | * | 3/1990 | Doi et al. ............... 382/130 |
| 4,984,286 A | * | 1/1991 | Dolazza ................. 382/263 |
| 5,151,869 A | | 9/1992 | Alcala |
| 5,196,709 A | | 3/1993 | Berndt et al. |
| 5,414,623 A | * | 5/1995 | Lu et al. ................. 382/131 |
| 5,482,041 A | * | 1/1996 | Wilk et al. .............. 600/430 |
| 5,485,530 A | * | 1/1996 | Lakowicz et al. ........ 382/191 |
| 5,784,157 A | * | 7/1998 | Gorfinkel et al. ........ 356/318 |
| 6,032,070 A | * | 2/2000 | Flock et al. ............. 600/473 |
| 6,192,322 B1 | * | 2/2001 | Rafanelli et al. ......... 702/150 |
| 6,272,374 B1 | * | 8/2001 | Flock et al. ............. 600/473 |
| 6,353,673 B1 | * | 3/2002 | Shnitser et al. .......... 382/103 |
| 6,771,798 B1 | * | 8/2004 | Grossman et al. ....... 382/103 |
| 6,975,899 B2 | | 12/2005 | Faupel et al. |
| 7,006,861 B2 | * | 2/2006 | Flock et al. ............. 600/473 |
| 7,336,810 B2 | * | 2/2008 | Fujii et al. .............. 382/128 |
| 7,599,732 B2 | * | 10/2009 | Sevick-Muraca et al. .... 600/476 |

(Continued)

FOREIGN PATENT DOCUMENTS

WO    2006135769 A1    12/2006

(Continued)

OTHER PUBLICATIONS

Tumor—Backgrounds, Robin N Strikeland, IEEE, 0278-0062, 1994, pp. 491-499.*

*Primary Examiner* — Jayesh A Patel
(74) *Attorney, Agent, or Firm* — Jason K. Klindtworth

(57) ABSTRACT

A method of fluorescence imaging is provided. The method provides for simultaneously acquiring image data at a plurality of phases and a plurality of frequencies from a region of interest, identifying at least one desired signal and at least one background signal in the acquired image data associated with the region of interest, constructing a digital filter based upon the at least one desired signal and the at least one background signal, wherein the digital filter is configured to enhance image contrast and applying the digital filter to the acquired image data associated with the region of interest to enhance image contrast in the acquired image data. Systems and computer programs that afford functionality of the type defined by this method are also provided.

14 Claims, 3 Drawing Sheets

U.S. PATENT DOCUMENTS

| | | | |
|---|---|---|---|
| 7,792,321 B2 * | 9/2010 | Palmadesso et al. | 382/100 |
| 2002/0072677 A1 * | 6/2002 | Sevick-Muraca et al. | 600/473 |
| 2004/0059218 A1 * | 3/2004 | Kanda et al. | 600/437 |
| 2004/0208390 A1 | 10/2004 | Jiang et al. | |
| 2005/0085732 A1 | 4/2005 | Sevick-Muraca et al. | |
| 2006/0023948 A1 * | 2/2006 | Palmadesso et al. | 382/191 |
| 2006/0149479 A1 | 7/2006 | Ma | |
| 2007/0197894 A1 | 8/2007 | Jo et al. | |

FOREIGN PATENT DOCUMENTS

| | | |
|---|---|---|
| WO | 2007038679 A2 | 4/2007 |
| WO | 2007143141 A2 | 12/2007 |
| WO | WO2007143141 A2 * | 12/2007 |

* cited by examiner

SYSTEM AND METHOD FOR CONTRAST ENHANCEMENT OF TIME-RESOLVED FLUORESCENCE IMAGES

BACKGROUND

Embodiments of the invention relate generally to imaging and more particularly to contrast enhancement of time-resolved fluorescence images.

In modern healthcare facilities, non-invasive imaging systems are often used for identifying, diagnosing, and treating physical conditions. Medical imaging encompasses different non-invasive techniques used to image and visualize the internal structures and/or functional behavior (such as chemical or metabolic activity) of organs and tissues within a patient. Currently, a number of modalities exist for medical diagnostic and imaging systems, each typically operating on different physical principles to generate different types of images and information. These modalities include ultrasound systems, computed tomography (CT) systems, X-ray systems (including both conventional and digital or digitized imaging systems), positron emission tomography (PET) systems, single photon emission computed tomography (SPECT) systems, and magnetic resonance (MR) imaging systems.

Further, fluorescence imaging techniques typically utilize differences in the fluorescence response of normal tissue and abnormal tissue, such as in the detection and localization of cancer. Fluorophores that are excited during fluorescence endoscopy may be exogenously applied agents that accumulate preferentially in disease associated tissues, or they may be the endogenous fluorophores that are present in all tissue. In the latter case, the fluorescence from the tissue is typically referred to as autofluorescence. Tissue autofluorescence is typically due to fluorophores with absorption bands in the ultraviolet and blue portion of the visible spectrum and certain emission bands in the green to red portions of the visible spectrum. In tissue states associated with early cancer, the green portion of the autofluorescence spectrum is appreciably suppressed. This spectral difference between disease and healthy tissue may be used to distinguish normal tissue from suspicious tissue.

Moreover, fluorescence detection offers one of the most sensitive methods for quantification of probe molecules in biological and material systems because it can attain near single-molecule sensitivity levels. Consequently, this technique is widely used in the assaying of biochemical and cellular systems, and in particular the microscopic imaging of cell-based assays, where rich biological information is provided from multiplexed high-content data.

In addition, fluorescence imaging can enhance the contrast between different fluorophores present in tissue or exogenous fluorescent dyes used during clinical and preclinical operations. The field of view and overall speed of the imaging system are critical requirements for real-time and/or high-throughput imaging applications. Existing methods, such as time correlated single photon counting (TCSPC) or frequency domain phase sensitive detection (FDPSD) often face difficulty in acquiring and displaying the processed image data fast enough for practical use. Moreover, in conventional frequency domain lifetime imaging the modulation frequency must be changed to obtain multi-frequency phase information which may lead to longer imaging time and slower image update rates.

It is therefore desirable to have an improved multi-frequency modulation scheme for high-speed frequency domain phase sensitive detection of fluorescence and also permit rapid excitation and collection of time-resolved multi-frequency fluorescence data from a wide field of view.

BRIEF DESCRIPTION

Briefly in accordance with one aspect of the technique a method of fluorescence imaging is provided. The method provides for simultaneously acquiring image data at a plurality of phases and a plurality of frequencies from a region of interest, identifying at least one desired signal and at least one background signal in the acquired image data associated with the region of interest, constructing a digital filter based upon the at least one desired signal and the at least one background signal, wherein the digital filter is configured to enhance image contrast and applying the digital filter to the acquired image data associated with the region of interest to enhance image contrast in the acquired image data. Systems and computer programs that afford that afford functionality of the type defined by this method may be provided by the present technique.

In accordance with another aspect of the technique a fluorescent imaging platform is provided. The fluorescent imaging platform comprises a multi-frequency signal generator for generating multi-frequency waveforms at a plurality of frequencies and a plurality of phases, a high speed imager for simultaneously acquiring image data from a region of interest at the plurality of frequencies and the plurality of phases. Further, the imaging platform comprises a computer configured to construct a digital filter based upon at least one desired signal and at least one background signal, wherein the digital filter is configured to enhance image contrast and apply the digital filter to the acquired image data associated with the region of interest to suppress background signals while enhancing desired signals in the acquired image data to generate data with enhanced image contrast.

In accordance with yet another aspect of the technique a fluorescent imaging system is provided. The fluorescent imaging system comprises a light source for illuminating a medium with a multi-frequency excitation light, an emission filter for blocking emission light wavelengths from the light source, an excitation filter for blocking excitation light wavelengths from the medium. The fluorescent imaging system comprises a fluorescent imaging platform, comprising a multi frequency signal generator for generating multi-frequency waveforms at a plurality of frequencies and a plurality of phases, a high speed imager for simultaneously acquiring image data from a region of interest at the plurality of frequencies and the plurality of phases and a computer configured to construct a digital filter based upon at least one desired signal and at least one background signal, wherein the digital filter is configured to enhance image contrast and apply the digital filter to the acquired image data associated with the region of interest to generate data with enhanced image contrast.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
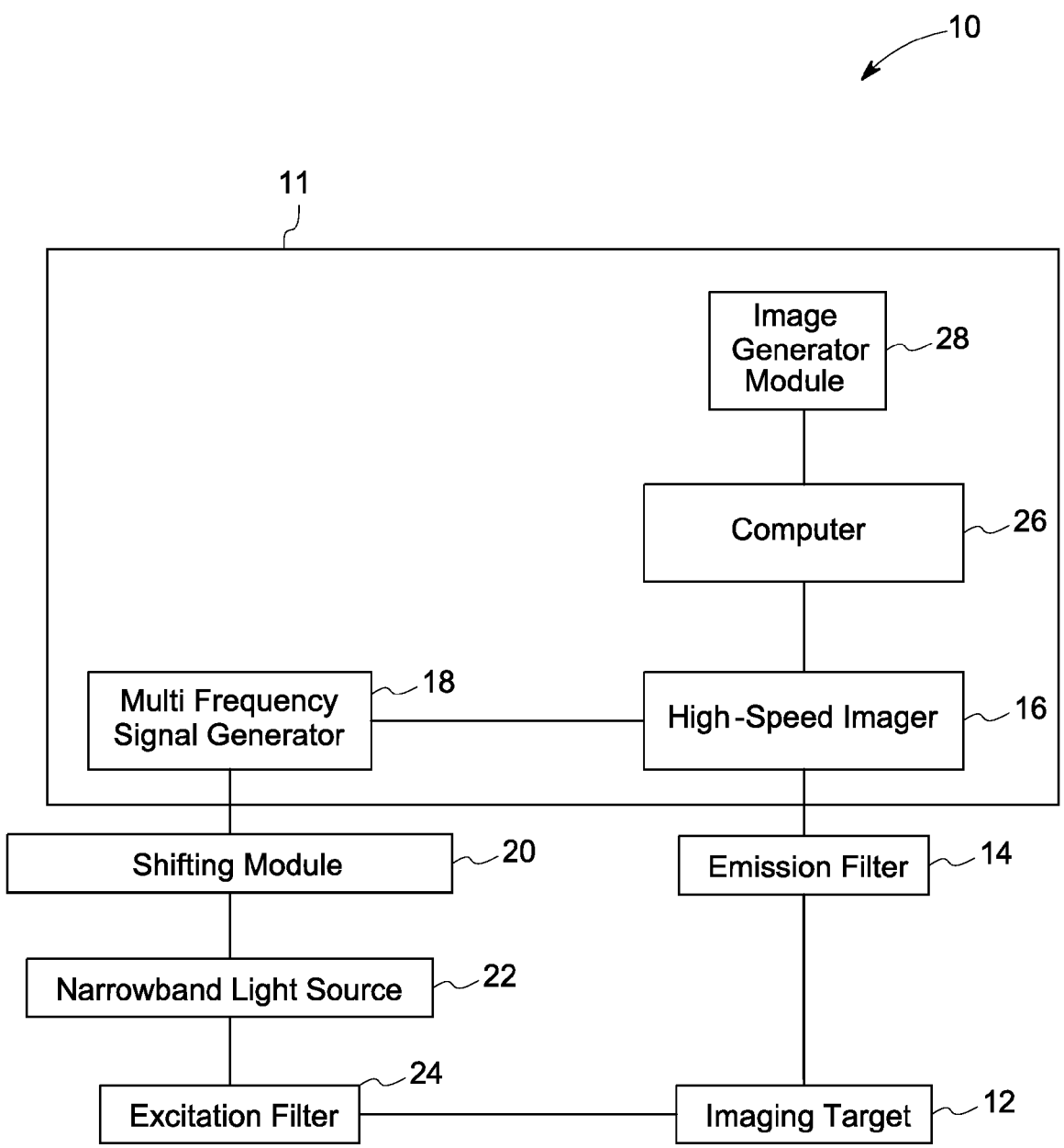
FIG. 1 is a block diagram of a fluorescent imaging system according to aspects of the present technique.

Embodiments of the present invention relate to a fluorescent imaging system for enhancement of image contrast. Referring to FIG. 1, a fluorescent imaging system 10 is presented. The fluorescent imaging system 10 is configured to deliver an intensity-modulated excitation light onto tissue of an imaging target 12 to cause emission of light in the fluorescent wavelengths. Emission light from the imaging target 12 may be detected by a high-speed imager 16. In one embodiment, the high-speed imager 16 may include a charged-coupled device (CCD) camera (not shown in FIG. 1) and an image intensifier (not shown in FIG. 1). This high-speed imager 16 may be configured to produce images of the imaging target 12 based on the wavelengths of the light emitted by the imaging target 12.

With continuing reference to FIG. 1, the imaging system 10 may also include a multi-frequency signal generator 18, which may be configured to generate multiple radiofrequency (RF) waveforms. In one embodiment, the multi-frequency signal generator 18 may be configured to generate RF waveforms in a range from about 1 MHz to about 100 MHz. The RF waveforms may be phase shifted or time shifted via use of a shifting module 20 coupled to the multi-frequency signal generator 18. The multi-frequency signal generator 18 may be configured to drive a light source 22. Further, the light source 22 may be configured to produce a beam of excitation light for illuminating an area of the imaging target 12. In one embodiment, the excitation light stimulates the imaging target 12 that has had a fluorescent dye administered to it. By way of example, the imaging target 12 may be administered with a fluorescent dye, such as, but not limited to, methylene blue that emits light in response to the excitation light.

Furthermore, in one embodiment, this light source 22 may include a narrowband light source 22. Moreover, in another embodiment, the narrowband light source 22 may emit 670 nanometer excitation light provided by a 3 watt light emitting diode (LED) array. However, other suitable wavelengths and sources, such as, but not limited to, laser diodes may also be used. The narrowband light source 22 may include other light sources capable of emitting light in a narrowband that nearly matches the absorption spectrum of the administered dye, such as near infrared light. For example, the narrow band light source 22 may emit near infrared light in a range from about 770 nm to about 800 nm, which may match the absorption spectrum of indocyanine green dye.

The imaging system 10 may also include an excitation filter 24 configured to filter the energy of light emitted by the narrow band light source 22. The emission light emitted from the imaging target 12 includes light emitted as a result of the excitation light stimulating the fluorescent imaging target 12 and the autofluorescence of the tissue in the imaging target 12. An emission filter 14 may be employed to filter the wavelengths from the narrowband light source 22 that may also be reflected from the fluorescent imaging target 12. In accordance with aspects of the present technique, the LED excitation voltage in the narrow band light source 22 may be configured to not include a DC offset. It may be noted that having an offset means that the LED light output may include a larger static component to it that may cause both long-lifetime and short-lifetime fluorophores to emit continuously rather than decay according to their characteristic lifetime. The light released from the continuous emission is not useful and may only reduce the dynamic range of the imaging system.

As previously noted, the multi-frequency signal generator 18 is operationally coupled to the shifting module 20. In one embodiment the shifting module 20 may be configured to shift multi-frequency RF waveforms at a plurality of phases in the narrowband light source 22. It may be noted that the LED will only light with correct electrical polarity. In other words, when the voltage across the p-n junction in the LED is in a correct direction, a significant current flows and the LED is said to be forward biased or in an ON-state. However, if the voltage is of the wrong polarity, the LED is said to be reverse biased or in an OFF-state and no light is emitted. The LED may also be operated on an alternating current (AC) voltage, with the LED emitting light only with the positive voltage, causing the LED to turn ON and OFF at the frequency of the AC supply. During the OFF-phase of excitation, the excitation LEDs are reverse biased, thus the imaging target 12 emits only the fluorescent emission light. In certain other embodiments, the shifting module 20 may also be configured to change the frequency settings of the high-speed imager 16.

Furthermore, the imaging target 12 generates fluorescent light at a longer wavelength than the narrowband light source 22. This wavelength of light may be passed through the emission filter 14, which is configured to block the remaining wavelengths of light, such as that which is reflected from the imaging target. The emitted light that passes through the emission filter 14 is in turn detected by the high-speed imager 16. In one embodiment, the high-speed imager 16 may include a wide field area imager. Additionally, the high-speed imager 16 may include a detector (not shown) to detect the wavelengths of light emitted from the imaging target 12. It may also be noted that, in accordance with the aspects of the present technique, the gain of the high-speed imager 16 may be modulated by the multi-frequency signal generator 18.

Moreover, in one embodiment, the image intensifier (not shown in FIG. 1) may include a photocathode to convert photons to electrons and a display screen made of phosphorescent material that is capable of converting electrons into an optical image. A direct current (DC) bias may be applied via the image intensifier (not shown in FIG. 1) to enable modulation around a selectable optical gain.

With continuing reference to FIG. 1, the high-speed imager 16 and the narrowband light source 22 may be phase locked. Moreover, by employing the shifting module 20, relative phase between the narrowband light source 22 and the high-speed imager 16 may be changed in discrete steps during the acquisition of images resulting in acquisition of multiple phase images. Similarly, multiple images may be acquired by changing time or frequency settings. Moreover, a combination of multiple images may be acquired by changing the phase and time or frequency settings.

Furthermore, the excitation light waveform contains multiple harmonics that result from the non-linear electro-optic properties of the LEDs. It may be noted that the LEDs have inherent multi-frequency output due to their non-linear electro-optic properties such as, for example, rectification of excitation power. The use of multi-frequency excitation enables simultaneous collection of multi-frequency fluorescence data, which may increase measurement throughput and decrease imaging time of the imaging system 10.

In accordance with further aspects of the present technique, the imaging system 10 includes an imaging platform 11. In one embodiment, the imaging platform 11 may be a fluorescent imaging platform. The fluorescent imaging platform 11 includes the high-speed imager 16 and the multi-frequency signal generator 18. The fluorescent imaging platform 11 may also include a computer 26 and an image generator module 28. In one embodiment, the image generator module 28 may be implemented in hardware. Alternatively, the image generator module 28 may be implemented as software and it could be integrated as a part of the imaging platform 11.

In the embodiment illustrated in FIG. 1, the image generator module 28 may be operatively coupled to the computer 26. Alternatively, the image generator module 28 may be a part of the computer 26. In addition, the image generator module 28 may be configured to generate images based on the data acquired by the high-speed imager 16. The computer 26 may also be configured to construct a digital filter that may be employed to enhance the contrast of the fluorescent images, according to aspects of the present technique. It may be noted that the digital filter constructed by the computer 26 is different from the emission filter 14 and the excitation filter 24 (see FIG. 1). The implementation of the digital filter will be described in greater detail with respect to FIG. 2 and FIG. 3.

Moreover, the imaging system 10 may also include a storage unit (not shown in FIG. 1) that may be used to store data. In one embodiment, the storage unit may include memory configured to store the image data. It should be understood that any type of computer accessible memory device capable of storing the desired amount of data and/or code may be utilized by such an exemplary imaging system 10. Furthermore, the storage unit may include one or more memory devices, such as magnetic, solid state, or optical devices, of similar or different types, which may be local and/or remote to the system 10. The storage unit may store data, processing parameters, and/or computer programs including one or more routines for performing the processes described herein.

Figure 2:
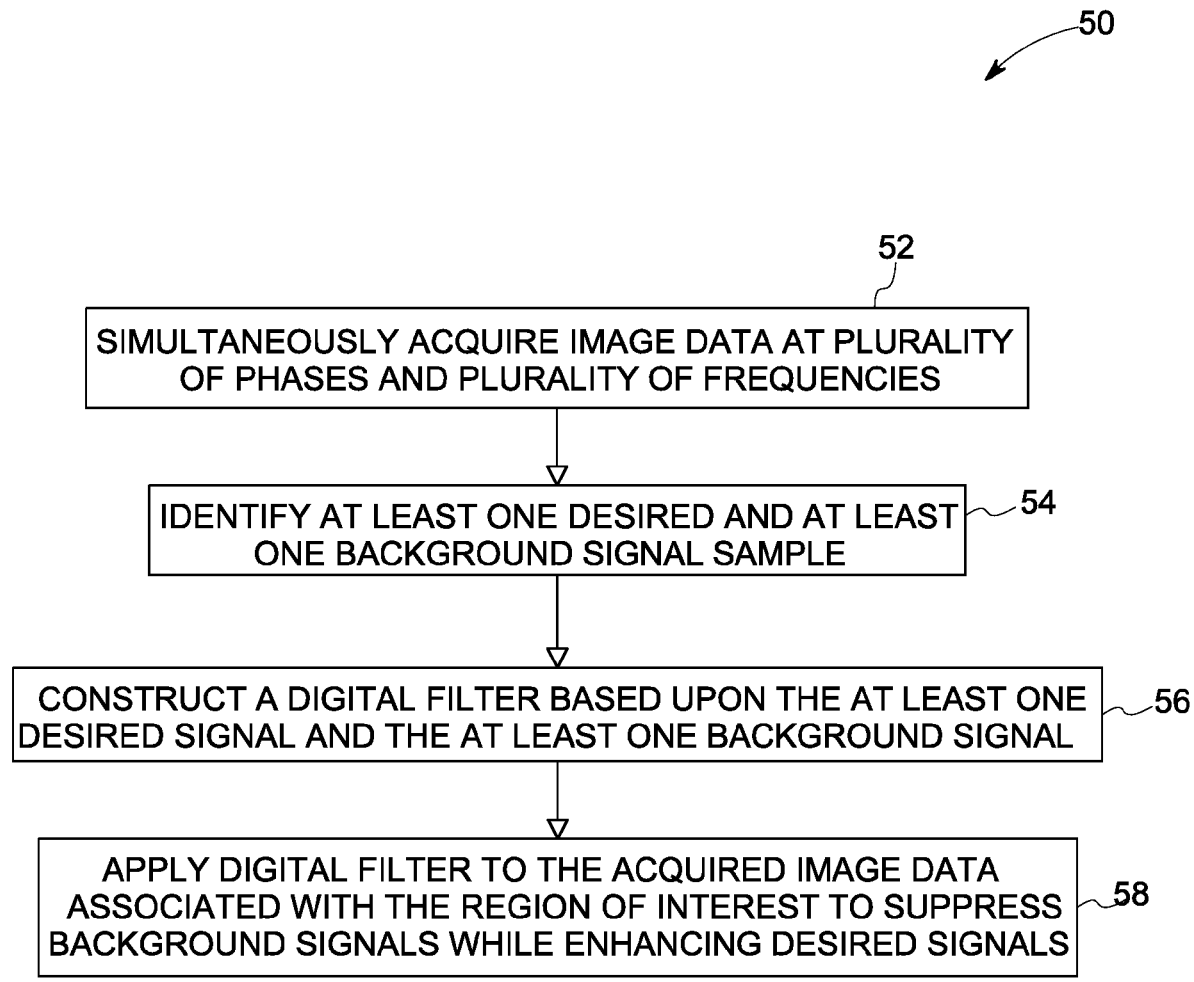
FIG. 2 is a flow chart illustrating an exemplary method of imaging, according to an aspect of the present technique.

Turning now to FIG. 2, a flowchart 50 illustrating an exemplary method of imaging according to aspects of the present technique is depicted. The method starts at step 52 where image data may be acquired by a high-speed imager such as the high-speed imager 16 (see FIG. 1). More particularly, in accordance with exemplary aspects of the present technique, image data may be simultaneously acquired by the high-speed imager 16 at a plurality of phases and a plurality of frequencies. It may be noted that each of the multiple images acquired may include a corresponding set of pixels. These sets of pixels may have different intensity values for different phase shifts and different time shifts. Furthermore, the acquired image data may include one or more background signals, one or more desired signals and other data signals representative of a region of interest in an object, such as a patient for example.

Subsequently, at step 54, at least one background signal or undesired signal and at least one desired signal from a region of interest are identified. In one embodiment, the desired signal and the background signal may be identified for example by, injecting a contrast agent that selectively targets a cancerous tumor. In this case, the tumor is a source for desired signals and a healthy region of the body, for example, a portion of the skin, serves as the source of background signals. The desired signals and background signals may then be acquired by imaging the two regions using the same set of frequencies and/or phases and gating settings. The desired and background signal samples may thereafter be represented in a form of vectors. It may be noted that the vectors may include background vectors and signal vectors.

Additionally, at step 56, a digital filter may be constructed based upon the at least one desired signal and the at least one background signal, where the digital filter may be configured to aid in separating the desired signals from the background signals based on the differences between the characteristics of the background signals and the desired signals. In certain embodiments, it may be noted that the digital filter created at step 56 may be implemented in software. The working of this filter will be explained in greater detail with reference to FIG. 3.

The undesired signals that may be associated with the region of interest may then be filtered, as indicated by step 58. More particularly, the digital filter is applied to the acquired image data associated with the region of interest to suppress the undesired signal characteristics such as background signals while enhancing the desired signals as in step 58 to enhance image contrast in the acquired image data.

Figure 3:
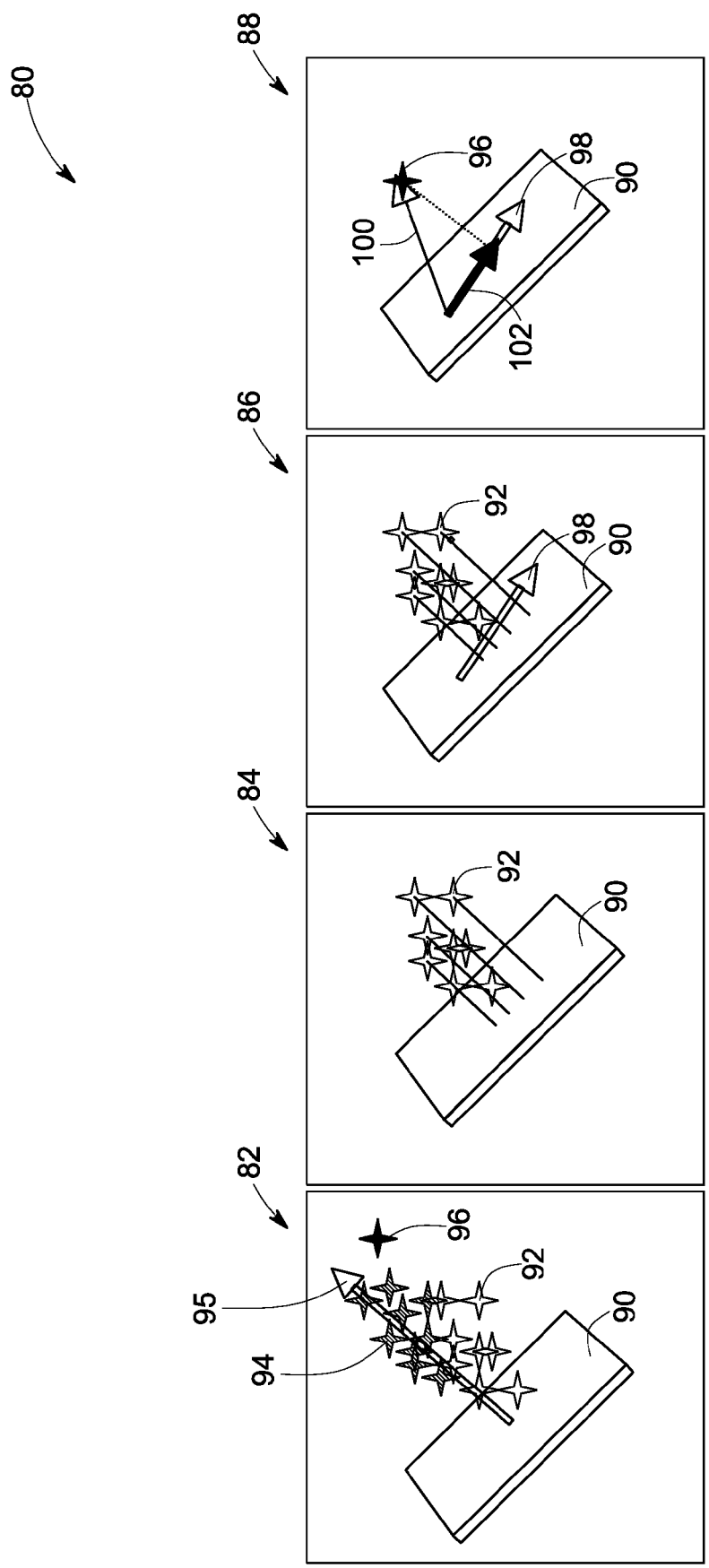
FIG. 3 is a diagram illustrating projection of signal and background vectors, according to an aspect of the present technique.

Referring now to FIG. 3, a diagrammatic illustration 80 of the method of imaging is described with regard to FIG. 2. Panel 82 is representative of background signal samples 94, desired signal samples 92 and other data signals 96 obtained at multiple frequency and phase settings by the high-speed imager 16 of FIG. 1. A background signal vector 95 may be formed using the background signal samples 94. Further, reference numeral 90 may be indicative of background orthogonalized null space 90 of the background signal samples 94. Also, panel 84 illustrates projection of the desired signal data samples 92 into the background orthogonalized null space 90. Thereafter, panel 86 illustrates a matched filter 98 that may be constructed based on the projection of the desired signal data samples to the background orthogonalized null space 90. This matched filter 98 may be configured to filter background signal characteristics from the desired signal data samples 92. Panel 88 illustrates other data signal vector 100 formed using the other data signal samples 96. The other data signal vector 100 may thereafter be projected to the background orthogonalized null space 90 where the matched filter 98 may be used to project the other data signal vector 100 to obtain a filtered data vector 102. It may be noted that the matched filter 98 is illustrative of the digital filter described with regard to FIG. 2. The computation described hereinabove collapses the set of data vectors into a set of scalar values, where the magnitude of each value is positive but less than or equal to the magnitude of the data vector before projection. Thus, the projected data vector magnitudes represent the degree of similarity between the data vectors and the background orthogonalized signal vectors.

According to aspects of the present technique the high-speed imager 16 (see FIG. 1) may be configured to acquire a plurality of image datasets. In one embodiment, two sets of data vectors may be selected from a region of interest in a set of fluorescence images. Alternatively, the data vectors may be selected from repeated measurements on the imaging target. The data vector may be representative of the variation of the fluorescence measurement as a function of a set of controlled fluorescence parameters such as, but not limited to, lifetime, phase shift, frequency, excitation wavelength, emission wavelength, polarization and so forth. Additionally, the data vectors may be of any length and may contain any combination of time domain, frequency domain or spectral characteristics of the fluorescent emission.

Furthermore, according to other aspects of the present technique, the desired signals and the background signals may be selectively enhanced and attenuated, respectively. In certain embodiments, a background data matrix may be formed, which is a collection of data from a region of the image that is known to contain little or no desired signals. Each column of the background data matrix includes data from a single pixel in the region collected with different gating, phase shift or frequency settings on the imager 16 (see FIG. 1). In one embodiment, the principal components of the background data matrix may be computed employing a variety of algorithms such as, but not limited to, singular value decomposition. The n-largest principal components of the background data matrix may then be selected and used to calculate a projection matrix into the space spanned by the background vectors. The n-largest principal components may be selected based on singular values before the discontinuity of the singular value distribution for the background data matrix. Choosing 'n' larger than this value will increase background signal suppression at the expense of signal to noise ratio in the processed results. Thus, if 'n' is too small, the background signals will not be suppressed and the contrast between the background and signal vectors will not be significantly enhanced. Conversely, if 'n' is too large, the contrast may be large but the signal to noise ratio may be small. For example, the value of 'n' may be chosen between 3 and 20. It may however be noted that the value of 'n' is dependent on the number of phase/frequency permutations, and increases as the phase/frequency permutations are increased. More particularly, the value of 'n' may be close to the location of the discontinuity in a plot of the singular value distribution.

The methods and systems of fluorescence imaging as described hereinabove may also be referred to as time-resolved fluorescence imaging and have several advantages such as contrast enhancement of time-resolved fluorescence images. Further, the techniques advantageously provide for reducing effects of variable or unknown measurement noise, tissue scattering, temporal response functions of excitation sources and detectors and multi-exponential decay phenomena in fluorescence lifetime data analysis. This processing scheme may greatly improve the contrast between signal and background regions of the image and improve the signal to noise ratio in the signal regions.

The foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code, as will be appreciated by those of ordinary skill in the art, may be stored or adapted for storage on one or more tangible, machine readable media, such as on memory chips, local or remote hard disks, optical disks (that is, CDs or DVDs), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of fluorescence imaging comprising:
simultaneously acquiring image data at a plurality of phases and a plurality of frequencies from a region of interest, wherein the acquired image data comprises at least one of one or more background signals, one or more desired signals, and other data signals;
identifying at least one desired signal and at least one background signal in the acquired image data associated with the region of interest;
constructing a customized digital filter based upon the at least one desired signal and the at least one background signal, wherein the customized digital filter is configured to enhance image contrast, said customized digital filter further comprising representing the one or more background signals and the one or more desired signals in the form of vectors to obtain background signal vectors and desired signal vectors respectively and protecting the desired signal vectors to a background orthogonalized null-space associated with the background signals; and
applying the customized digital filter to the acquired image data associated with the region of interest to enhance image contrast in the acquired image data.

2. The method of claim 1, wherein image data is acquired by a high-speed imager.

3. The method of claim 1, wherein the at least one desired signal and the at least one background signal are representative of a variation of fluorescence measurement as a function of one or more fluorescence parameters.

4. The method of claim 3, wherein the one or more fluorescence parameters comprise a lifetime, a phase shift, a frequency, an excitation wavelength, a detection wavelength and polarization.

5. The method of claim 1, wherein applying the customized digital filter to the acquired image data associated with the region of interest comprises suppressing the background signals while enhancing the desired signals in the acquired image data.

6. The method of claim 1, wherein applying the customized digital filter comprises filtering background signal characteristics from the desired signals.

7. The method of claim 6, further comprising projecting the other data signals to the background orthogonalized null-space.

8. The method of claim 7, further comprising filtering the projected other data signals via use of the customized digital filter to generate a filtered data vector.

9. A fluorescent imaging platform, comprising:
a multi-frequency signal generator for generating multi-frequency waveforms at a plurality of frequencies and a plurality of phases;
a high speed imager for simultaneously acquiring image data from a region of interest at the plurality of frequencies and the plurality of phases, wherein the acquired image data comprises at least one of one or more background signals, one or more desired signals, and other data signals;
a computer configured to:
construct a customized digital filter based upon at least one desired signal and at least one background signal, wherein the customized digital filter is configured to enhance image contrast, said customized digital filter further comprising representing the one or more background signals and the one or more desired signals in the form of vectors to obtain background signal vectors and desired signal vectors respectively and projecting the desired signal vectors to a background orthogonalized null-space associated with the background signals; and
apply the customized digital filter to the acquired image data associated with the region of interest to suppress background signals while enhancing desired signals in the acquired image data to generate data with enhanced image contrast.

10. The fluorescent imaging platform of claim 9, further comprising a shifting module configured to shift multi-frequency waveforms at the plurality of phases.

11. The fluorescent imaging platform of claim 9, further comprising an image generator module configured to generate an image using the data with enhanced image contrast.

12. A fluorescent imaging system, comprising:
- a light source for illuminating a medium with a multi-frequency excitation light;
- an emission filter for blocking emission light wavelengths from the light source;
- an excitation filter for blocking excitation light wavelengths from the medium;
- a fluorescent imaging platform, comprising: a multi frequency signal generator for generating multi-frequency waveforms at a plurality of frequencies and a plurality of phases;
- a high speed imager for simultaneously acquiring image data from a region of interest at the plurality of frequencies and the plurality of phases, wherein the acquired image data comprises at least one of one or more background signals, one or more desired signals, and other data signals;
- a computer configured to:
  - construct a customized digital filter based upon at least one desired signal and at least one background signal, wherein the customized digital filter is configured to enhance image contrast, said customized digital filter further comprising representing the one or more background signals and the one or more desired signals in the form of vectors to obtain background signal vectors and desired signal vectors respectively and projecting the desired signal vectors to a background orthogonalized null-space associated with the background signals; and
  - apply the customized digital filter to the acquired image data associated with the region of interest to generate data with enhanced image contrast.

13. The fluorescent imaging system of claim 12, further configured to suppress the one or more background signals while enhancing the one or more desired signals in the acquired image data.

14. The fluorescent imaging system of claim 12, further configured to filter background signal characteristics from the one or more desired signals.

* * * * *